(12) United States Patent
Sonesson et al.

(10) Patent No.: US 7,579,474 B2
(45) Date of Patent: Aug. 25, 2009

(54) SUBSTITUTED PIPERIDINES AS MODULATORS OF DOPAMINE NEUROTRANSMISSION

(75) Inventors: Clas Sonesson, Billdal (SE); Lars Swanson, Öjersjö (SE); Nicholas Waters, Göteborg (SE)

(73) Assignee: NSAB, Filial AF Neurosearch AB, Sverige, Ballerup (DK)

( * ) Notice: Subject to any disclaimer, the term of this patent is extended or adjusted under 35 U.S.C. 154(b) by 0 days.

(21) Appl. No.: 11/567,886

(22) Filed: Dec. 7, 2006

(65) Prior Publication Data

US 2007/0270467 A1 Nov. 22, 2007

Related U.S. Application Data

(63) Continuation of application No. PCT/EP2005/006152, filed on Jun. 8, 2005.

(60) Provisional application No. 60/577,767, filed on Jun. 8, 2004.

(30) Foreign Application Priority Data

Jun. 8, 2004 (SE) .................................. 0401465

(51) Int. Cl.
C07D 211/00 (2006.01)
(52) U.S. Cl. ..................................... 546/217
(58) Field of Classification Search ................. 546/217
See application file for complete search history.

(56) References Cited

U.S. PATENT DOCUMENTS

| | | | |
|---|---|---|---|
| 3,326,916 A | 6/1967 | Creighton et al. | |
| 3,539,573 A | 11/1970 | Schmutz et al. | |
| 4,048,314 A * | 9/1977 | Kubela et al. ............ | 514/235.5 |
| 4,202,898 A | 5/1980 | Depoortere | |
| 4,333,942 A | 6/1982 | Eistetter et al. | |
| 4,415,736 A | 11/1983 | Ciganek et al. | |
| 4,485,109 A * | 11/1984 | Ciganek ..................... | 514/317 |
| 4,504,660 A | 3/1985 | Klaubert et al. | |
| 5,462,947 A | 10/1995 | Svensson et al. | |
| 5,502,050 A | 3/1996 | Gross | |
| 6,175,015 B1 | 1/2001 | Yuan et al. | |
| 6,924,374 B2 * | 8/2005 | Sonesson et al. ............ | 546/192 |
| 2003/0109532 A1 | 6/2003 | Sonesson et al. | |

FOREIGN PATENT DOCUMENTS

| | | |
|---|---|---|
| EP | 0060179 | 2/1982 |
| EP | 0369887 | 11/1989 |
| EP | 0094159 | 4/1990 |
| EP | 0533267 | 9/1992 |
| EP | 0867183 | 10/2004 |
| GB | 1060160 | 7/1965 |
| WO | 9109594 | 7/1991 |
| WO | 9218475 | 10/1992 |
| WO | 9300313 | 1/1993 |
| WO | 9304684 | 3/1993 |
| WO | 9811068 | 3/1998 |
| WO | WO 0146145 | 6/2001 |
| WO | WO 0146146 | 6/2001 |
| WO | 02059108 | 8/2002 |
| WO | 2005121087 | 12/2005 |
| WO | 2005121088 | 12/2005 |
| WO | 2006039325 | 4/2006 |
| WO | 2006040155 | 4/2006 |
| WO | 2006040156 | 4/2006 |
| WO | 2007042295 | 4/2007 |
| WO | 8905799 | 6/2007 |
| WO | 2007065655 | 6/2007 |

OTHER PUBLICATIONS

Radl et al. STN Accession No. 1999:661865 Document No. 132:35590, Abstract of Journal of Heterocyclic Chemistry (1999), 36(4), 1017-1022.*
Rosenfeld et al. STN Accession No. 1977:60610, Document No. 86:60610 Abstract of, Journal of Chromatography (1976),129, 387-92.*
Author Unknown; Chapter 17 "Mind-Altering Drugs"; Psychopharmacology: Raven Press, New York, NY; pp. 731, 762 and 763.
Roth et al.,; Chapter 21, "Biochemical Pharmacology of Midbrain Dopamine Neurons" Departments of Pharmacology and Psychiatry, Yale University School of Medicine; New Haven, Connecticut; pp. 227 and 237.
Moore et al.,; Chapter 22, "Dopaminergic Neuronal Systems in the Hypothalamus"; Department of Pharmacology and Toxicology, Michigan State University, East Lansing, Michigan; pp. 245 and 254.
Michael Le Moal; Chapter 25, "Mesocorticolimbic Dopaminergic Neurons Functional and Regulatory Roles"; Psychchobiologie des Comportements Adaptatifs, Brodeaux, France; pp. 283 and 292.
Philip Seeman; Chapter 26, "Dopamine Receptors Clinical Correlates"Departments of Pharmacology and Psychiatry, University of Toronto, Toronto, Ontario, Canada; pp. 295-301.
George F. Koob; Chapter 66, "Animal Models of Drug Addiction" Department of Neuropharmacology: La Jolla, California; pp. 759-760.

(Continued)

*Primary Examiner*—D. Margaret Seaman
*Assistant Examiner*—Nizal S Chandrakumar
(74) *Attorney, Agent, or Firm*—Gauthier & Connors LLP

(57) ABSTRACT

The present invention relates to compounds having therapeutic effects against disorders in the central nervous system, and in particular substituted hydroxypiperidines of the formula 1:

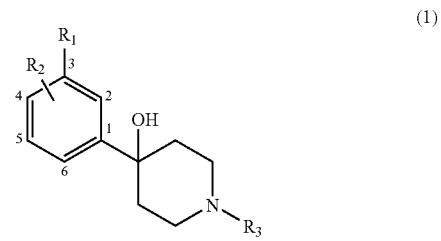

(1)

wherein R1, R2, and R3 are as defined herein.

6 Claims, No Drawings

OTHER PUBLICATIONS

Sato et al,.: "Oxidation of fulfides to sulfoxcides and sulfones with 30% hydrogen peroxide under organic solvent-and-halogen-free conditiona"; Department of Chemistry and Research Center for Materials Science, Nagoya University, Chikusa Nagoya, Japan: pp. 2469-2476.

Coyle et al., "Alzheimer's Disease: A Disorder of Cortical Cholinergic Innervation", John Hopkins School of Medical Science, vol. 219; gs. 1184-1190.

Author Unknown; "Effect of Chemical Structure on Antipsychotic Activity:; Burger's Medicinal Chemistry"; pp. 872-873.

Feldman et al., Principles of Neuropsychopharmacology; Chapter 17; "Mind Altering Drugs" 1997, pp. 731, 762-763.

Roth et al., "Biochemical Pharmacology of Midbrain Dopamine Neurons" Psychopharmacology: The Fourth Generation of Progress, Raven Press Ltd.; New York; Chapter 21, 1995, pp. 227 & 237.

Moore et al., "Dopamineregic Neuronal Systems in the Hypothalmus"; Department of Pharmacology & Toxicology; Michigan State University; East Lansing, Michigan; he Fourth Generation of Progress, Raven Press Ltd.; New York; Chapter 22, 1995, pp. 245 & 254.

Moal, "Mesocorticolimbic Dopaminergic Neurons" Psychopharmacology: The Fourth Generation of Progress, Raven Press Ltd.; New York; Chapter 25, 1995, pp. 283-292.

Seeman, "Dopamine Receptors" Psychopharmacology: The Fourth Generation of Progress, Raven Press Ltd.; New York; Chapter 26, 1995, pp. 295-301.

Koob, "Animal Models of Drug Addiction" Psychopharmacology: The Fourth Generation of Progress, Raven Press Ltd.; New York; Chapter 66, 1995, pp. 759-760.

Sato et al., "Oxidation of Sulfides to sulfoxides and sulfones with 30% hydrogen peroxide under organic solvent-and-halogen-free conditions" Department of Chemistry and Research Center for Materials Science, Nagoya University, Tetrahedron 57 (2001) pp. 2469-2476.

Coyle et al., "Alzheimer's Disease: A Disorder of Cortical Cholinergic Innervation" John Hopkins School of Medical Science, vol. 219, Mar. 11, 1983, pp. 1184-1190.

Wolff, Manfred E., Burger's Medicinal Chemistry-4th Edition, Part III; John Wiley & Sons 1979, pp. 872-873.

* cited by examiner

SUBSTITUTED PIPERIDINES AS MODULATORS OF DOPAMINE NEUROTRANSMISSION

PRIORITY

The present application is a continuation of PCT Application No. PCT/EP2005/006152 filed on Jun. 8, 2005 which claims priority to U.S. Provisional Application Ser. No. 60/577,767, filed on Jun. 8, 2004, and Swedish Application No. SE 0401465-0, filed on Jun. 8, 2004, all of which are incorporated herein by reference in their entirety.

FIELD OF THE INVENTION

The present invention relates to new modulators of dopamine neurotransmission, and more specifically to new substituted piperidines, and use thereof.

BACKGROUND OF THE INVENTION

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly, at central dopamine receptors are commonly used in the treatment of neurological and psychiatric disorders, e.g. Parkinson's disease and schizophrenia. However, currently available dopaminergic pharmaceuticals may have severe side effects. For instance, dopamine antagonists are known to induce both motor (extrapyramidal side effects; EPS) and mental side effects (e.g. anhedonia, dysphoria, and impairment of cognition), and dopaminergic agonists are known to induce dyskinesias and psychoses (Goodman and Gilman's the Pharmacological Basis of Therapeutics, 9th ed./McGraw-Hill, USA. Chapter 18, p 407-416, Chapter 22, p 509-512, p 515-516). An approach adopted by many researchers to improve efficacy and reduce side effects of dopaminergic pharmaceuticals, is to develop novel dopamine receptor ligands with selectivity at specific dopamine receptor subtypes or with regional selectivity. Yet another class of compounds acting through the dopamine systems of the brain are dopaminergic stabilizers, which have shown to be useful in the treatment of both neurologic and psychiatric disorders (A. Ekesbo, PhD Thesis, Uppsala University, Sweden: Functional consequences of dopaminergic degeneration; clinical and experimental studies using a novel stabilizer of dopaminergic systems: Ekesbo et al, (−)-OSU6162 inhibits levodopa-induced dyskinesias in a monkey model of Parkinson's disease, *Neuroreport*, 8, 2567, 1997; Tedroff et al. Long-lasting improvement in motor function following (−)-OSU6162 in a patient with Huntington's disease. *Neurology*, 22; 53:1605-6, 1999; Gefvert O. et al, (−)-OSU6162 induces a rapid onset of antipsychotic effect after a single dose. A double-blind placebo-controlled pilot study. *Scandinavian Society for Psychopharmacology*, 41$^{st}$ Annual Meeting, Copenhagen Denmark Nordic Journal of Psychiatry 54/2 93-94, April 2000: Carlsson et al, *Annu. Rev. Pharmacol. Toxicol.*, 41, 237, 2001; Carlsson et al. *Current Medicinal Chemistry*, 11, 267, 2004).

Another dopaminergic compound, which has been referred to as a dopamine-serotonin system stabiliser, as well as a partial DA $D_2$ receptor agonist, is the recently launched antipsychotic compound aripiprazole (Burris et al, *Pharm. Exp. Ther*, vol. 302, 381, 2002). Furthermore, compounds referred to as dopaminergic stabilizers have been described in WO01/46145, WO01/46146, Pettersson et al. The development of ACR16. A new class of dopaminergic stabilizers. *Society for Neuroscience* 32$^{nd}$ Annual Meeting, Abstract 2002, Vol. 28 part 1 1028, Orlando USA 2002; and Nyberg et al Efficacy and tolerability of the new dopamine stabiliser ACR16 a randomised placebo-controlled add-on study in patients with schizophrenia 12th BIENNIAL WINTER WORKSHOP ON SCHIZOPHRENIA, 7-13 Feb. 2004, Davos, Switzerland.

The typical pharmacological effects that are characteristic for dopaminergic stabilizers as described in WO01/46145, WO01/46146 and Pettersson et al. 2002 can be summarised as: 1) Increased turnover of dopamine in the terminal areas of the ascending dopaminergic projections of the mammalian brain; 2) No or only weak behavioural effects in otherwise untreated rats; and 3) Inhibition of behavioural effects induced by psychostimulants or psychotomimietic compounds in the rat. In the present invention this is referred to as a dopaminergic stabilizer profile.

It is known that certain pharmaceutically active compounds which are used in the treatment of neurological and psychiatric disorders (especially antipsychotic and antidepressant compounds) may have undesirable effects on those cardiac potassium channels which are involved in the electric repolarisation of cardiac cells, commonly referred to as hERG channels (human ether-a-go-go related gene encoded voltage-de-pendent potassium channel) or $I_{Kr}$ (rapidly activating delayed rectifier potassium current) channels. Drugs which block these channels can induce ventricular arrhythmia (Torsade de Pointes, TdP), leading to sudden death in otherwise healthy subjects. Indication that a drug might have undesirable effects on cardiac repolarisation is seen through prolongation of the QT interval of the electrocardiogram, which is considered to be a surrogate marker for risk of TdP. A number of drugs have been withdrawn from the market due to unacceptable side effects relating to cardiac arrhythmia (J. Cardiovasc. Electrophysiol. 15, 475, 2004; Eur. 1. Pharm., 450, 37, 2002; Cardiovascular Research, 58, 32, 2003)

This invention relates to the field of treatment of mammals suffering from CNS disorders in which the symptoms can be affected by dopaminergic functions, where the treatment comprises administering to said mammal an amount of a new type of compound, with a dopaminergic stabilizer profile. In addition, the compounds display low affinity at cardiac potassium channels, reducing the risk of serious cardiac side effects:

DESCRIPTION OF PRIOR ART

Compounds belonging to the class of substituted 4-(phenyl)-N-alkyl-piperidines have been previously reported. Among these compounds, some are inactive in the CNS, some display serotonergic or mixed serotonergic/dopaminergic pharmacological profiles while some are full or partial dopamine receptor agonists or antagonists with high affinity for dopamine receptors.

A number of 4-phenylpiperidine derivatives are known. EP0369887 disclose substituted 4-(meta-trifluoromethylphenyl)-1,2,3,6-tetrahydropyridines for treatment of anxiety. WO00/03713 discloses a method for the treatment of schizophrenia and other dopamine system dysfunctions by using substituted 1-methyl-4-phenyl-1,2,3,6-tetrahydropyridines.

WO96/06081 discloses neuroprotective phenol derivatives of formula:

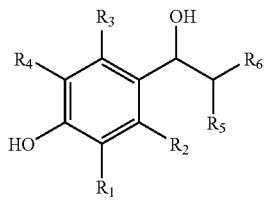

in which R6 may be a 4-aryl-4-hydroxy-substituted piperidine moiety. Such compounds are useful in the treatment of CNS degenerative diseases, among others.

WO02/090362 discloses compounds of the formula

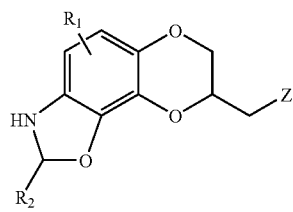

in which Z may be a 4-aryl-4-hydroxy-substituted piperidine moiety. Such compounds have affinity for brain $5\text{-HT}_{1A}$ serotonin receptors and are useful in the treatment of cognitive dysfunction, such as CNS disorders and schizophrenia.

WO97/23216 discloses 4-substituted piperidine analogues with the formula:

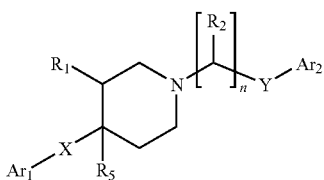

in which R5 may be selected from OH, and Ar1 may be substituted. Such compounds are used for treating CNS trauma, psychosis and neurodegenerative disorders, among others, through selective blockade of NMDA receptor subtypes.

U.S. Pat. No. 4,485,109 discloses compounds with formula:

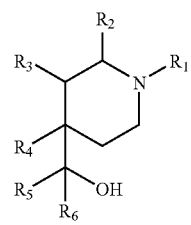

which are used as psychotherapeutic agents, particularly as antidepressants.

EP 1177792 discloses, among others, compounds with the structure:

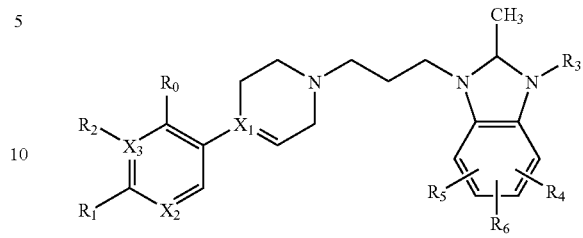

having dopaminergic activity—particularly as D4 receptor ligands—and useful for the treatment of novelty-seeking disorders.

EP 0846683 discloses 4-hydroxypiperidine derivatives of the formula:

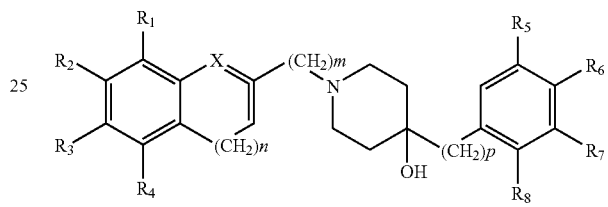

which selectively block NDMA (N-methyl-D-aspartate)-receptor subtypes and may be used in the treatment of neurodegenerative diseases.

U.S. Pat. No. 4,415,736 discloses compounds with the structure:

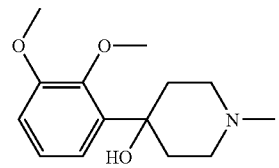

Such compounds are synthesis intermediates for the synthesis of tetrahydropyridine intermediates.

WO98/51668 discloses substituted piperidine derivatives of the formula:

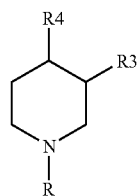

which possess properties as monoamine neurotransmitter i.e. dopamine, serotonin, noradrenaline, reuptake inhibitors. The compounds are said to be useful in the treatment of parkinsonism, depression, pseudodementia, obesity, narcolepsy, drug addiction, and/or abuse, attention-deficit hyperactivity disorders, senile dementia or memory dysfunctions.

In addition, it is known that compounds with formulae II (WO01/46145) and III (WO01/46146) possess dopaminergic stabilizer properties.

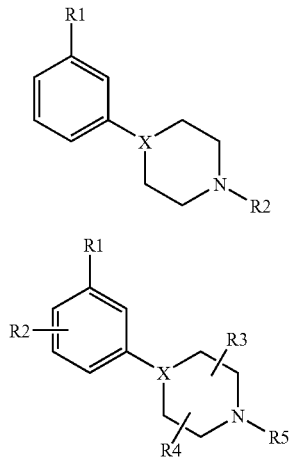

Formula II

Formula III

In formula II;

X is, inter alia, CH, $R_1$ is selected from the group consisting of $OSO_2CF_3$, $OSO_2CH_3$, $SOR_3$, $SO_2R_3$, $COR_3$, CN, $NO_2$, $CONHR_3$, $CF_3$ (proviso X is CH or C) F, Cl, Br, I (wherein $R_3$ is as specified below);

$R_2$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_4$ (wherein $R_4$ is as specified below);

$R_3$ is selected from the group consisting of $C_1$-$C_3$ alkyl, $CF_3$, or $N(R_2)_2$;

$R_4$ is selected from the group consisting of $C_3$-$C_6$ cycloalkyl, 2-tetrahydrofurane, 3-tetrahydrofuran.

In formula III;

X is, inter alia, CH, $R_1$ is selected from the group consisting of $OSO_2CF_3$, $OSO_2CH_3$, $SOR_7$, $SO_2R_7$, $COR_7$, CN, $NO_2$, $CONHR_3$, $CF_3$, F, Cl, Br, I (wherein $R_3$ is as specified below), 3-thiophene, 2-thiophene, 3-furane, 2-furane;

$R_2$ is selected from the group consisting of F, Cl, Br, I, CN, $CF_3$, $CH_3$, $OCH_3$, OH, $NH_2$ $R_3$ and $R_4$ are independently H or $C_1$-$C_4$ alkyl $R_5$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_6$;

$R_6$ is selected from the group consisting of $C_3$-$C_6$ cycloalkyl, 2-tetrahydrofurane, 3-tetrahydrofurane.

$R_7$ is selected from the group consisting of $C_1$-$C_3$ alkyl, $CF_3$ or $N(R_4)_2$ However, neither WO01/46145 (Formula II) nor WO01/46146 (Formula III) disclose substitution in the piperidine ring disclosed in the present invention. However, the following structures are known as synthesis intermediates in WO01/46146.

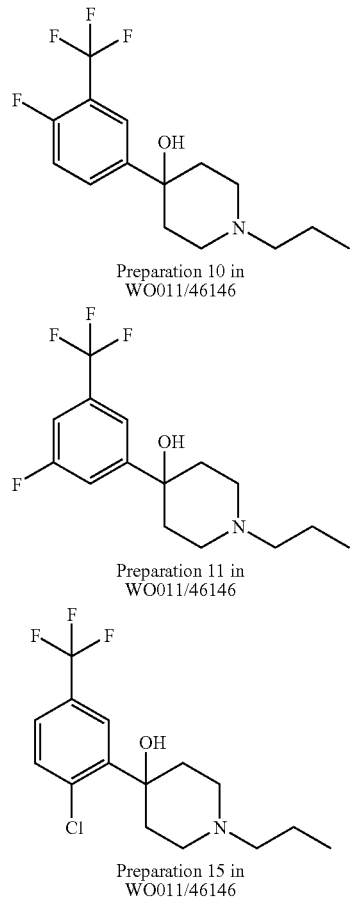

Preparation 10 in WO011/46146

Preparation 11 in WO011/46146

Preparation 15 in WO011/46146

In addition, none of these two patent applications discloses 2,3-disubstitution of the aryl ring, and it can be seen that alternative substitution patterns (e.g. 3,4-disubstitution in which the 4-position is halogen) or mono substituted (3-position) do not yield as potent compounds as the 2,3-disubstitution disclosed in the present invention. Furthermore, the introduction of the hydroxyl group on the piperidine ring in the present invention surprisingly improved the potency and efficacy. There remains a need for new pharmaceutically active compounds, especially useful in treatment of disorders in the central nervous system, having increased potency as dopaminergic stabilisers. It is also desirable that any such pharmaceutically active compound has reduced propensity for side effects, particularly as regards cardiac arrhythmia.

SUMMARY OF THE INVENTION

The object of the present invention is to provide new pharmaceutically active compounds, especially useful in treatment of disorders in the central nervous system, having increased potency as dopaminergic stabilisers (See Table 1 and 4) and a low propensity to block the hERG channel (see Table 1). These compounds have particular advantages with respect to reduced side effects, particularly cardiac side effects.

The substances according to the present invention have been biologically tested in the rat where they have been found to act preferentially on dopaminergic systems in the brain. They have effects on biochemical indices in the brain with the characteristic features of dopamine antagonists. However, the substances according to the invention show no, or only limited, inhibitory effects on spontaneous locomotion over a wide dose range. Further, the substances according to the invention can induce a slight behavioural activation, in particular when baseline locomotor activity is low. However, the substances in the present invention inhibit the behavioural activation induced by psychostimulants and psychotomimetics.

The substances according to the present invention display a low potency at inhibiting the hERG channel, as measured by IC50 in a Rb+ efflux assay (Development and evaluation of high throughput functional assay methods for hERG potassium channel. Tang W, Kang 1, Wu X, Rampe D, Wang L, Shen H, Li Z, Dunnington D, Garyantes T. *J Biomol Screen.* 2001 October; 6(5):325-31), indicating a low risk for QT interval prolongation and arrhythmia in man.

DETAILED DESCRIPTION OF THE INVENTION

The present invention relates to new piperidines in the form of free base or pharmaceutically acceptable salts thereof, pharmaceutical compositions containing said compounds and use of said compounds in the manufacture of pharmaceuticals being dopamine neurotransmitters and therapy.

More precisely, the present invention relates to piperidine compounds of Formula 1:

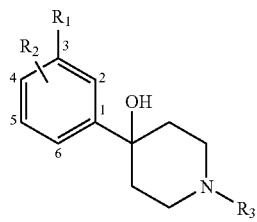

(1)

wherein:
R$_1$ is selected from the group consisting of OSO$_2$CF$_3$, OSO$_2$CH$_3$, OCF$_3$, OCHF$_2$, SCF$_3$, SCHF$_2$, SOR$_4$, SOR$_2$R$_4$, COR$_4$, CN, CF$_3$, F, Cl, Br, and I;
R$_2$ occupies either the 2-position or the 4-position in the phenyl ring;
when R$_2$ occupies the 2-position, R$_2$ is selected from the group consisting of H, OH, NH$_2$, F, Cl, and CH$_3$,
when R$_2$ occupies the 4-position, R$_2$ is selected from the group consisting of H, CN, CF$_3$, OH, NH$_2$, OR$_5$, F, Cl, Br, I, and CH$_3$,
R$_3$ is selected from the group consisting of C$_1$-C$_4$ alkyls, allyl, CH$_2$CH$_2$OCH$_3$, CH$_2$CH$_2$CH$_2$F, CH$_2$CH$_2$CHF$_2$ CH$_2$CH$_2$F, CH$_2$CHF$_2$ CH$_2$CF$_3$, 3,3,3-trifluoropropyl, and 4,4,4-trifluorobutyl;
R$_4$ is selected from the group consisting of C$_1$-C$_3$ alkyls, CN, CF$_3$, and CHF$_2$;

and pharmaceutically acceptable salts thereof.

Known compounds within this frame of compounds are those in which
R$_1$ is trifluoromethyl, R$_2$ is hydrogen and R$_3$ is methyl,
R$_1$ is trifluoromethyl, R$_2$ is 4-chloro and R$_3$ is methyl,
R$_1$ is trifluoromethyl, R$_2$ is 4-fluoro and R$_3$ is n-propyl.

In particular embodiments R$_1$ is selected from the group consisting of OSO$_2$CF$_3$, OSO$_2$CH$_3$, SO$_2$CF$_3$, COCF$_3$, CN, CF$_3$, and OCF$_3$. In other particular embodiments R$_1$ is selected from the group consisting of F, C$_1$ and CF$_3$. In other particular embodiments R$_2$ is selected from the group consisting of F or Cl. In other particular embodiments R$_3$ is selected from the group consisting of n-propyl and ethyl. In other particular embodiments R$_2$ occupies the 2-position of the phenyl ring. In other particular embodiments R$_2$ selected from the group consisting of F and Cl and R$_3$ is selected from the group consisting of n-propyl and ethyl.

The calculated octanol/water partitioning constant value (ClogP) influences the choice of compounds. Particularly of interest are compounds in which the calculated octanol/water partitioning constant value (ClogP) is greater than 1.0.

Another aspect of the invention relates to the use of the piperidine compounds of Formula 1:

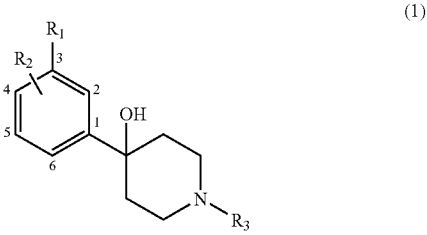

(1)

wherein:
R$_1$ is selected from the group consisting of OSO$_2$CF$_3$, OSC$_2$H$_3$, OCF$_3$, OCHF$_2$, SCF$_3$, SCHF$_2$, SOR$_4$, SO$_2$R$_4$, COR$_4$, CN, CF$_3$, F, Cl, Br, and I;
R$_2$ occupies either the 2-position or the 4-position in the phenyl ring;
when R$_2$ occupies the 2-position, R$_2$ is selected from the group consisting of H, OH, NH$_2$, F, Cl, and CH$_3$,
when R$_2$ occupies the 4-position, R$_2$ is selected from the group consisting of H, CN, CF$_3$, OH, NH$_2$, OR$_5$, F, Cl, Br, I, and CH$_3$,
R$_3$ is selected from the group consisting of C$_1$-C$_4$ alkyls, allyl, CH$_2$CH$_2$OCH$_3$, CH$_2$CH$_2$CH$_2$F, CH$_2$CH$_2$CHF$_2$ CH$_2$CH$_2$F, CH$_2$CHF$_2$ CH$_2$CF$_3$, 3,3,3-trifluoropropyl, and 4,4,4-trifluorobutyl;
R$_4$ is selected from the group consisting of C$_1$-C$_3$ alkyls, CN, CF$_3$, and CHF$_2$;

or a pharmaceutically acceptable salt thereof in the manufacture of pharmaceutically active preparations for treating a disorder of the central nervous system.

A further aspect of the invention relates to a method for treating central nervous system disorders by administering a therapeutically active amount of the compounds of formula 1 or a pharmaceutically acceptable salt thereof to a mammal, including human, suffering from a central nervous system disorder. Additionally, the present invention relates to a method for treating any disorders listed herein, by administering a therapeutically active amount of the compounds of formula 1 or a pharmaceutically acceptable salt thereof to a mammal, including human, suffering from said disorder.

Inclusion of two substituents on the aryl ring of such compounds—one in the 2-position (ortho) and the other in the 3-position (meta)—increases their potency in modulating dopamine neurotransmission. The unprecedented increase in potency of these 2,3-disubstituted compounds as compared to the mono-substituted, or the 3,4-disubstituted compounds is illustrated in TABLES 1 and 4. Compounds having 3,5 or 3,6-substitution patterns are not of interest in the present invention—indeed comparative example 10 proved to be inactive (TABLE 1). It has also been found that the introduction of a substituent in the piperidine ring improves the potency (compare comparative example 5 with example 11).

In addition, inclusion of a hydroxy substituent in the piperidine ring is found to decrease side effects relating to cardiac arrhythmia, as measured by the effect of these compounds on the hERG potassium channel (Rb efflux method). The unprecedented reduction in side effects of such substituted compounds—when compared with similar compounds without a substituent in the piperidine ring—is illustrated in TABLE 1.

Table 1: Estimated $ED_{50}$ values for the increase of DOPAC (3,4-dihydroxyphenylacetic acid) in the rat striatum after systemic administration of test compound and effect of test compound on Rb efflux through the hERG ion channel. For methods and statistical calculations see the enclosed tests.

|  | $ED_{50}$ DOPAC* µmol/kg | Rb efflux (IC50, nM) |
|---|---|---|
| Comparative examples | | |

|  | 9.0 (6.9-14) | 7970 |
|---|---|---|

1

|  | 41 (32-54) | 5660 |
|---|---|---|

2

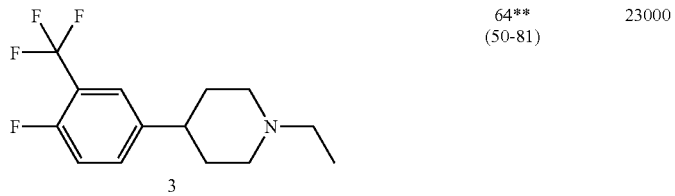

|  | 64** (50-81) | 23000 |
|---|---|---|

3

Claimed in WO01/46146

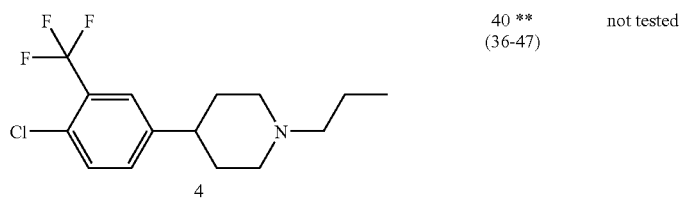

|  | 40 ** (36-47) | not tested |
|---|---|---|

4

Example 9 in WO01/46146

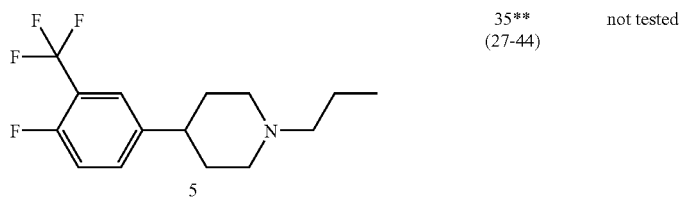

|  | 35** (27-44) | not tested |
|---|---|---|

5

Example 43 in WO01/46146

| | ED$_{50}$ DOPAC* μmol/kg | Rb efflux (IC50, nM) |
|---|---|---|
| 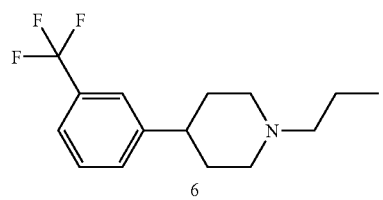<br>6<br>Example 4 in WO01/46145 | 84<br>(47-100) | not tested |
| 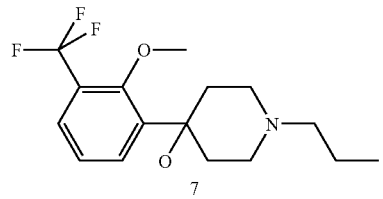<br>7 | Inactive*** | not tested |
| 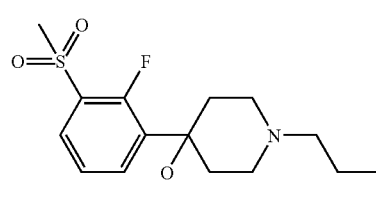<br>8 | Inactive*** | not tested |
| 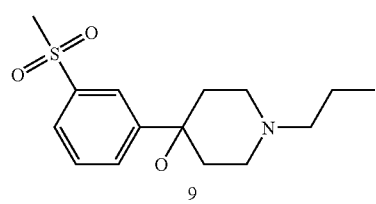<br>9 | Inactive*** | not tested |
| 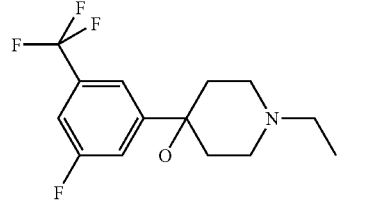<br>10 | Inactive*** | not tested |
| 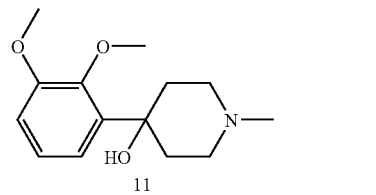<br>11<br>Example 1 and 2 in U.S. Pat. No. 4,415,736 | n.d**** | not tested |

-continued
| | ED$_{50}$ DOPAC* μmol/kg | Rb efflux (IC50, nM) |
|---|---|---|
Examples
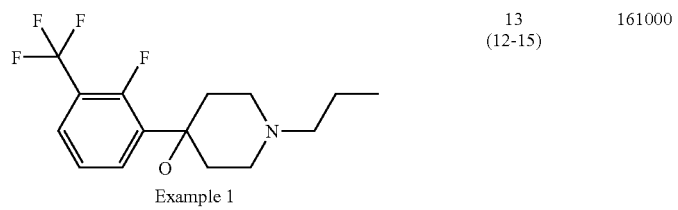
Example 1
13 (12-15)    161000
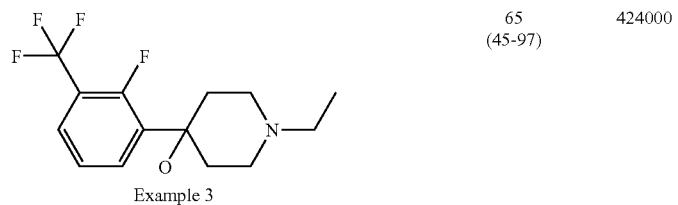
Example 3
65 (45-97)    424000
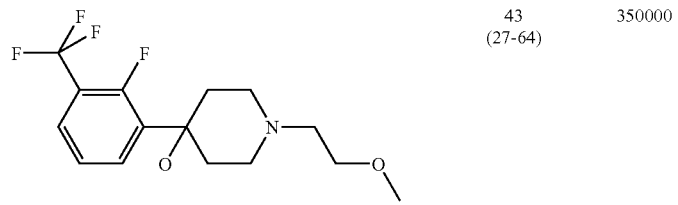
Example 4
43 (27-64)    350000
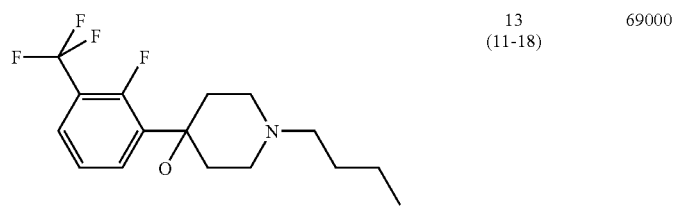
Example 5
13 (11-18)    69000
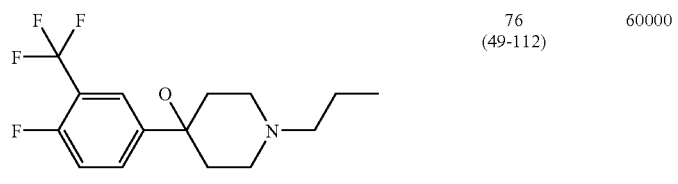
Example 8
76 (49-112)    60000
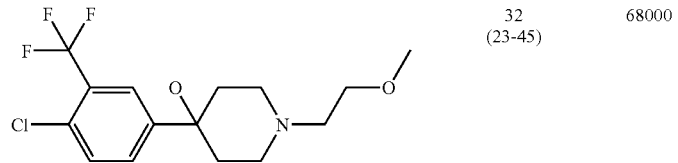
Example 2
32 (23-45)    68000

| | $ED_{50}$ DOPAC* μmol/kg | Rb efflux (IC50, nM) |
|---|---|---|
| 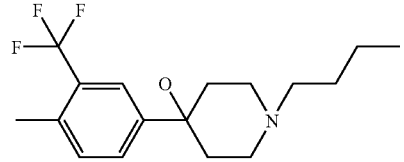<br>Example 9 | 56<br>(44-70) | not tested |

*in $ED_{50}$ estimates the maximal effects have been limited to 350-400% of control.
**in $ED_{50}$ estimates the maximal effects have been set to 200% of control (this is the maximal increase in DOPAC that is possible to achieve for these compounds).
***inactive at 100 μmol/kg
****not determined.; The $ED_{50}$ value was not possible to calculate because the compound did not reach sufficient high DOPAC levels after administration of 100 μmol/kg.

An important observation is that the presence of the OH substituent in the piperidine ring does not impair the efficacy or potency of the dopaminergic stabilizer, but only reduces inhibition of the hERG channel. Such an outcome would not have been predicted as a general rule. For instance, in the comparative examples 7-10, the presence of the OH-group leads to compounds which are devoid of dopamine stabilizer activity.

One aim of the present invention is to provide new compounds for therapeutic use, and more precisely compounds for modulation of dopaminergic systems in the mammalian brain, including human brain. Preferably such compounds have lowered side-effects with respect to cardiac potassium channel inhibition.

Another aim of the invention is to provide compounds with therapeutic effects after oral administration.

The preferred substituted structures are
4-(2,3-difluorophenyl)-1-propylpiperidin-4-ol
4-(2,3-difluorophenyl)-1-ethylpiperidin-4-ol
4-(2-chloro-3-fluorophenyl)-1-propylpiperidin-4-ol
4-(2-chloro-3-fluorophenyl)-1-ethylpiperidin-4-ol
4-[2-fluoro-3-(trifluoromethyl)phenyl]-1-propylpiperidin-4-ol
1-ethyl-4-[2-fluoro-3-(trifluoromethyl)phenyl]piperidin-4-ol
4-[2-chloro-3-(trifluoromethyl)phenyl]-1-propylpiperidin-4-ol
4-[2-chloro-3-(trifluoromethyl)phenyl]-1-ethylpiperidin-4-ol
4-(3-chloro-2-fluorophenyl)-1-propylpiperidin-4-ol
4-(3-chloro-2-fluorophenyl)-1-ethylpiperidin-4-ol
4-(2,3-dichlorophenyl)-1-propylpiperidin-4-ol
4-(2,3-dichlorophenyl)-1-ethylpiperidin-4-ol
4-[2-fluoro-3-(trifluoromethoxy)phenyl]-1-propylpiperidin-4-ol
1-ethyl-4-[2-fluoro-3-(trifluoromethoxy)phenyl]piperidin-4-ol
4-[2-chloro-3-(trifluoromethoxy)phenyl]-1-propylpiperidin-4-ol
4-[2-chloro-3-(trifluoromethoxy)phenyl]-1-ethylpiperidin-4-ol
4-[3-(difluoromethoxy)-2-fluorophenyl]-1-propylpiperidin-4-ol
4-[3-(difluoromethoxy)-2-fluorophenyl]-1-ethylpiperidin-4-ol
4-[2-chloro-3-(difluoromethoxy)phenyl]-1-propylpiperidin-4-ol
4-[2-chloro-3-(difluoromethoxy)phenyl]-1-ethylpiperidin-4-ol
4-(3,4-difluorophenyl)-1-propylpiperidin-4-ol
4-(3,4-difluorophenyl)-1-ethylpiperidin-4-ol
4-(4-chloro-3-fluorophenyl)-1-propylpiperidin-4-ol
4-(4-chloro-3-fluorophenyl)-1-ethylpiperidin-4-ol
2-fluoro-4-(4-hydroxy-1-propylpiperidin-4-yl)benzonitrile
4-(1-ethyl-4-hydroxypiperidin-4-yl)-2-fluorobenzonitrile
4-[4-fluoro-3-(trifluoromethyl)phenyl]-1-propylpiperidin-4-ol
1-ethyl-4-[4-fluoro-3-(trifluoromethyl)phenyl]piperidin-4-ol
4-[4-chloro-3-(trifluoromethyl)phenyl]-1-propylpiperidin-4-ol
4-[4-chloro-3-(trifluoromethyl)phenyl]-1-ethylpiperidin-4-ol
4-(4-hydroxy-1-propylpiperidin-4-yl)-2-(trifluoromethyl)benzonitrile
4-(1-ethyl-4-hydroxypiperidin-4-yl)-2-(trifluoromethyl)benzonitrile
4-(3-chloro-4-fluorophenyl)-1-propylpiperidin-4-ol
4-(3-chloro-4-fluorophenyl)-1-ethylpiperidin-4-ol
4-(3,4-dichlorophenyl)-1-propylpiperidin-4-ol
4-(3,4-dichlorophenyl)-1-ethylpiperidin-4-ol
2-chloro-4-(4-hydroxy-1-propylpiperidin-4-yl)benzonitrile
2-chloro-4-(1-ethyl-4-hydroxypiperidin-4-yl)benzonitrile
4-[4-fluoro-3-(trifluoromethoxy)phenyl]-1-propylpiperidin-4-ol
1-ethyl-4-[4-fluoro-3-(trifluoromethoxy)phenyl]piperidin-4-ol
4-[4-chloro-3-(trifluoromethoxy)phenyl]-1-propylpiperidin-4-ol
4-[4-chloro-3-(trifluoromethoxy)phenyl]-1-ethylpiperidin-4-ol
4-(4-hydroxy-1-propylpiperidin-4-yl)-2-(trifluoromethoxy)benzonitrile
4-(1-ethyl-4-hydroxypiperidin-4-yl)-2-(trifluoromethoxy)benzonitrile
4-[3-(difluoromethoxy)-4-fluorophenyl]-1-propylpiperidin-4-ol
4-[3-(difluoromethoxy)-4-fluorophenyl]-1-ethylpiperidin-4-ol
4-[4-chloro-3-(difluoromethoxy)phenyl]-1-propylpiperidin-4-ol
4-[4-chloro-3-(difluoromethoxy)phenyl]-1-ethylpiperidin-4-ol 2-(difluoromethoxy)-4-(4-hydroxy-1-propylpiperidin-4-yl) benzonitrile 2-(difluoromethoxy)-4-(1-ethyl-4-hydroxypiperidin-4-yl) benzonitrile The compounds and compositions according to the present invention possess dopamine-modulating properties and are useful in treating numerous central nervous system disorders, including both psychiatric and neurological disorders. Particularly, the compounds and their pharmaceutical compositions may be used in the treatment of CNS disorders where the dopaminergic system is dysfunctional due to direct or indirect causes.

The compounds and compositions according to the invention can be used to improve all forms of psychosis, including schizophrenia and schizophreniform disorders as well as drug induced psychotic disorders and bipolar disorder. They can also be used in the treatment of a condition selected from the group consisting of iatrogenic and non-iatrogenic psychoses and hallucinoses.

Mood and anxiety disorders, including depression and obsessive-compulsive disease may also be treated with the compounds and compositions according to the invention.

Compounds with modulating effects on dopaminergic systems may also be used to improve cognitive functions and in the treatment of emotional disturbances related to ageing, neurodegenerative (e.g. Dementia and age-related cognitive impairment) and developmental (such as Autism spectrum disorders, ADHD, Cerebral Palsy, Gilles de la Tourette's syndrome) disorders as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds, environmental toxins. The compounds and their pharmaceutical composition are useful for treatment of a condition selected from the group consisting of sleep disorders, sexual disorders, eating disorders, obesitas, and headaches and other pains in conditions characterized by increased muscular tone. They may also be used in the treatment of Alzheimer's disease or related dementia disorders.

The compounds and compositions according to the invention may also be used in behavioural disorders usually first diagnosed in infancy, childhood, or adolescence as well as in impulse control disorders.

They can also be used for treating substance abuse disorders as well as disorders characterized by misuse of food.

Neurological indications include the use of the compounds and their compositions to improve mental and motor function in Parkinson's disease, dyskinesias (including L-DOPA induced dyskinesias), and in related parkinsonian syndromes. They may also be used to ameliorate tics and tremor of different origins. Moreover, they may be used to relieve pain in conditions characterized by increased muscle tone.

They can also be used in the treatment of Huntington's disease and other movement disorders as well as movement disorders induced by drugs. Restless legs and related disorders as well as narcolepsy may also be treated with compounds according to the invention.

The compounds according to the present invention have been shown to display dopaminergic stabilizer profile with improved potency (Tables 1 and 4). They have effects on biochemical indices in the brain with the characteristic features of dopamine antagonists, e.g. producing increases in concentrations of dopamine metabolites.

The compounds of this invention show no, or only limited effects on spontaneous locomotion over a wide dose range (Table 2).

TABLE 2

Effects of compounds from the present invention on Locomotor activity in drug-naive rats. The animals were placed in the motility meters immediately after drug administration and locomotor activity was recorded for 60 minutes (counts/60 min ± SEM)

| | Control group | 11 µmol/kg | 33 µmol/kg | 100 µmol/kg |
|---|---|---|---|---|
| Example 3 | 10811 ± 865 | 7481 ± 1266 | 11085 ± 2020 | 11288 ± 1339 |
| Example 7 | 6421 ± 812 | 7229 ± 769 | 7669 ± 1029 | 7542 ± 844 |

TABLE 2-continued

Effects of compounds from the present invention on Locomotor activity in drug-naive rats. The animals were placed in the motility meters immediately after drug administration and locomotor activity was recorded for 60 minutes (counts/60 min ± SEM)

| | Control group | 11 μmol/kg | 33 μmol/kg | 100 μmol/kg |
|---|---|---|---|---|
| 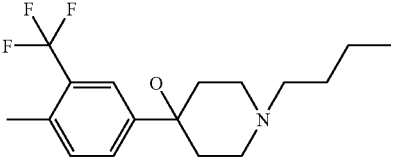 Example 9 | 7487 ± 1597 | 8188 ± 1055 | 2879 ± 503 | 2961 ± 928 |
| 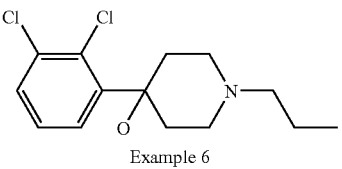 Example 6 | 9822 ± 3030 | 8897 ± 801 | 9739 ± 2025 | 7499 ± 1620 |
| 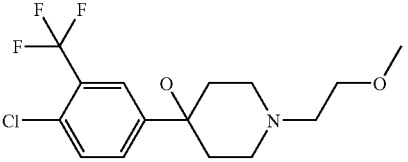 Example 2 | 9992 ± 1924 | 7945 ± 1230 | 5041 ± 2022 | 4493 ± 1081 |
| 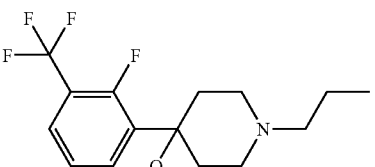 Example 1 | 12672 ± 702 | 11764 ± 3106 | 7506 ± 905 | 3698 ± 294 |
| 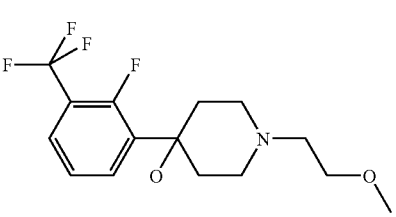 Example 4 | 8836 ± 962 | 6422 ± 1190 | 6016 ± 1708 | 4296 ± 847 |
| 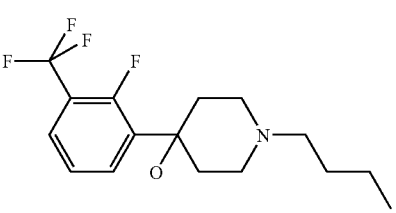 Example 5 | 7154 ± 2447 | 7668 ± 1716 | 3213 ± 825 | 1630 ± 302 |

TABLE 2-continued

Effects of compounds from the present invention on Locomotor activity in drug-naive rats. The animals were placed in the motility meters immediately after drug administration and locomotor activity was recorded for 60 minutes (counts/60 min ± SEM)

| | Control group | 11 μmol/kg | 33 μmol/kg | 100 μmol/kg |
|---|---|---|---|---|
| 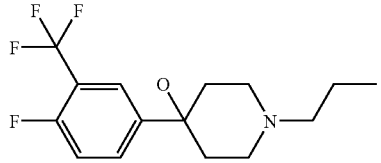 Example 8 | 6292 ± 808 | 6114 ± 1032 | 5906 ± 1340 | 5546 ± 441 |

In some cases, in particular when the baseline activity is low, they can induce a slight behavioural activation (Table 3). The behavioural activation is limited, not reaching the profound increases in activity induced by direct or indirect dopaminergic agonists. On the other hand, the preferred substances reduce the increase in activity induced by direct or indirect dopaminergic agonists, i.e. d-amphetamine and congeners (Table 4).

TABLE 3

Effects of compounds from the present invention on Locomotor activity in drug-naive rats. The animals were placed in the motility meters immediately after drug administration and locomotor activity was recorded between 30 and 60 minutes (counts/30 min ± SEM). During this period the animals have habituated to their environment and therefore the locomotor activity is low in the control group.

| | Control group | 11 μmol/kg | 33 μmol/kg | 100 μmol/kg |
|---|---|---|---|---|
| 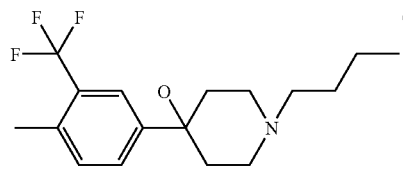 Example 9 | 625 ± 354 | 2092 ± 1437 | 1337 ± 141 | 1365 ± 460 |
| 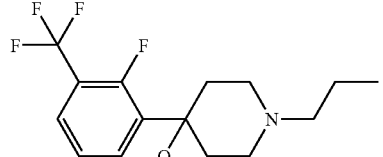 Example 1 | 281 ± 138 | 3200 ± 1817 | 1130 ± 344 (P = 0.06) | 541 ± 145 |
| 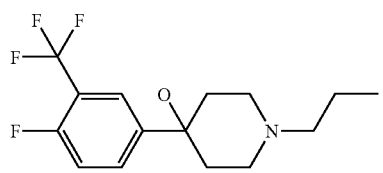 Example 8 | 104 ± 23 | 213 ± 180 | 436 ± 246 | 258 ± 134 |

TABLE 4

Effects of compounds in the present invention on reduction of amphetamine-induced hyper-locomotion. Comparative examples from prior art is also included. For methods and statistical calculations see the enclosed tests.

| Examples | ED$_{50}$ µmol/kg | Comparative Examples | ED$_{50}$ µmol/kg |
|---|---|---|---|
| 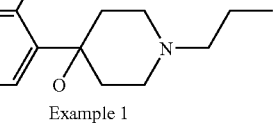 Example 1 | 15 (11-19) | 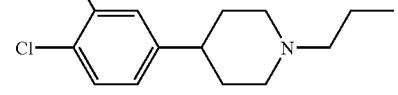 Example 9 in WO01/46146 | 34 (12-54)) |
|  Example 3 | 26 (16-41) |  Example 43 in WO01/46146 | 30 (21-44)) |
| 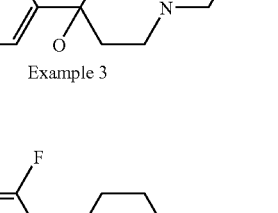 Example 4 | 21 (18-24) | 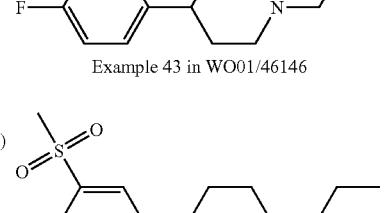 Example 6 in WO01/46145 | 52 (35-76) |
| 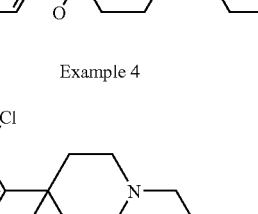 Example 6 | 25 (13-66) | 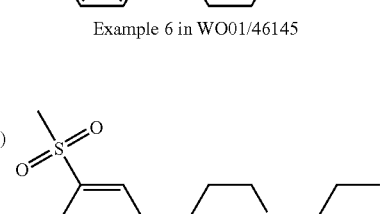 | inactive |
| 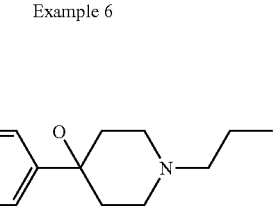 Example 8 | 21 (15-28) | 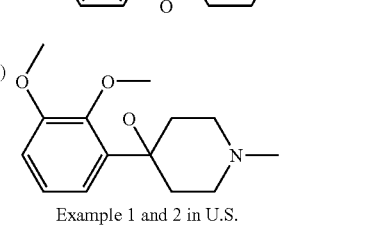 Example 1 and 2 in U.S. Pat. No. 4,415,736 | inactive |
| 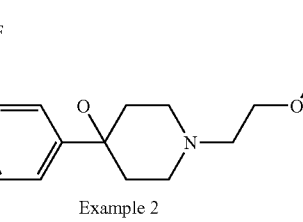 Example 2 | 20 (16-26) | | |

Thus, the compounds of this invention show a dopaminergic stabilizer profile (Tables 1-4) with improved or retained potency (Table 1 and 4) compared to the non-substituted piperidine ring analogue. In addition, the introduction of the hydroxyl group in the piperidine ring decreased the potency at inhibiting the HERG channel.

Given the involvement of dopamine in a large variety of CNS functions and the clinical shortcomings of presently available pharmaceuticals acting on dopamine systems, the novel class of dopaminergic modulators presented in this invention may prove superior to presently known dopaminergic compounds in the treatment of several disorders related to dysfunctions of the CNS, in terms of efficacy as well as reduced side effects.

The compounds in the present invention have also been shown to display high metabolic stability in rat liver microsomes measured as turnover at 15 minutes (Example 1 27%, Example 3 8%, Example 8 29%), and high oral bioavailability in rat, exemplified by Example 3 (around 80%) and Example 8 (around 29%).

These compounds are thus suitable for the preparation of orally administered pharmaceuticals. There is no guidance in the prior art how to obtain compounds with this effect on behaviour and dopamine systems in the brain.

Pharmacology

Evidence is available that dopaminergic neurotransmission in the CNS is disturbed in psychiatric and neurological diseases. In many instances, for example in schizophrenia, Parkinson's disease, Huntington's disease, bipolar disorder and in dementia pharmacotherapies based on antagonism or agonism at dopamine receptors are useful, but not optimal. In recent years many efforts have been made in finding novel and selective compounds for dopamine receptor subtypes (D1, D2, D3, D4, D5) with the aim to improve efficacy and reduce side effects.

The present invention offers another principle for novel therapeutics based on interactions with the dopamine system. The invention provides compounds having, as their major feature, stabilizing effects on the dopaminergic system in the brain.

Description of Animal Models Used in the Invention

The compounds according to the invention have effects on brain neurochemistry similar to antagonists at dopamine D2 receptors (i.e. dose-dependent increases of the dopamine metabolite DOPAC, in cortical, striatal and limbic brain regions). The compounds according to the invention show no, or only limited inhibitory, effects on spontaneous locomotion. Under certain conditions they can induce a behavioural activation. The behavioural activation is limited, not reaching the profound increases in activity induced by direct or indirect dopamine receptor agonists. However, the preferred substances reduce the increase in activity induced by the indirect dopaminergic agonist d-amphetamine. The increase in activity after treatment with d-amphetamine is a standard model of hyperdopaminergia (Table 4). In this model, dopaminergic neurotransmission is increased by systemic administration of d-amphetamine at a dose that is sufficiently high to produce a large increase in locomotor activity. The ability of a compound to antagonize this hyperactivity reflects anti-dopaminergic properties, which are part of the dopaminergic stabiliser profile. Furthermore, antagonism of d-amphetamine induced hyperactivity is widely used as a standard assay of antipsychotic activity (see Psychopharmacology 4th Generation of progress Chapter 68, p 793-795).

Another animal model of antipsychotic activity is based on administration of the glutamate antagonist MK-801. Glutamate antagonists (i.e. NMDA antagonists), can induce psychoses in man (see Psychopharmacology, 4th Generation of progress Chapter 101, p. 1205 and 1207) and induce behavioural aberrations in animals. Thus, the ability of a drug to affect schizophrenia and psychotic states can be measured using behavioural models based on experimentally induced hypoglutamatergic states. In this study the NMDA antagonist MK-801 (0.7 mg/kg i.p.) was used to create a hypoglutamatergic state where the rats display abnormal, hyperactive behaviour. Compounds in the present invention dose-dependently reverse the behavioural aberration induced by MK-801 (see Table 5).

It is known that the dopaminergic systems of the brain interacts strongly with other transmitter systems (see Psychopharmacology, 4th Generation of progress, Chapter 101, pages 1208-1209). Such interactions can explain the powerful effects of dopaminergic stabilizers on the behavioural aberrations induced by the glutamate antagonist MK-801 although these aberrations are not primarily based on or caused by changes in dopaminergic transmission.

TABLE 5

Effects of compounds from the present invention on Locomotor activity in MK-801 pre-treated rats (0.7 mg/kg i.p. 90 minutes before test compound). The animals were placed in the motility meters immediately after test compound administration and locomotor activity was recorded between 30 and 60 minutes after administration (counts/30 min ± SEM)

|  | Control group | MK-801 0.7 mg/kg i.p. | MK + example 100 µmol/kg |
|---|---|---|---|
| 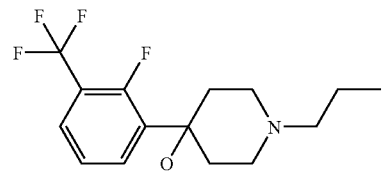 Example 1 | 46 ± 29 | 40367 ± 9127 | 17802 ± 6842 (P = 0.09) |
| 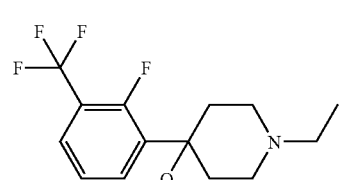 Example 3 | 125 ± 48 | 32169 ± 10605 | 18307 ± 7375 (P = 0.3) |

TABLE 5-continued

Effects of compounds from the present invention on Locomotor activity in MK-801 pre-treated rats (0.7 mg/kg i.p. 90 minutes before test compound). The animals were placed in the motility meters immediately after test compound administration and locomotor activity was recorded between 30 and 60 minutes after administration (counts/30 min ± SEM)

| | Control group | MK-801 0.7 mg/kg i.p. | MK + example 100 µmol/kg |
|---|---|---|---|
| 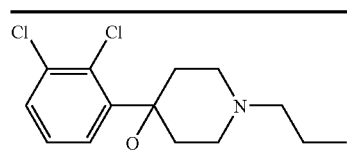 Example 6 | 341 ± 201 | 30819 ± 12771 | 9564 ± 4584 (P =0.16) |
| 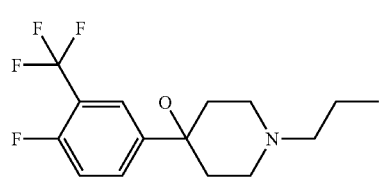 Example 8 | 547 ± 162 | 42061 ± 2219 | 7312 ± 4537 (P =0.0005) |
| 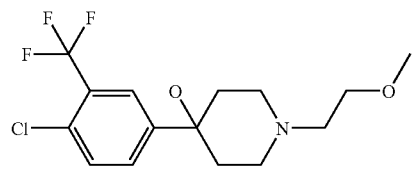 Example 2 | 1106 ± 693 | 58370 ± 3007 | 7407 ± 3282 (P =0.00003) |

Therapeutic Use of Dopaminergic Stabilizers

The claimed invention provides compounds having, as their major feature, stabilizing effects on the dopaminergic system in the brain. These compounds are useful for treating CNS disorders in which the symptoms can be affected by dopaminergic functions. In support of this assertion, please see the following references:

In support of schizophrenia and psychosis, Applicants refer to Psychopharmacology 4th
Generation of progress Chapter 26, p. 295-301);
Parkinson's disease (Psychopharmacology 4th Generation of progress Chapter 26, p 295, Chapter 1479-1482);
Anxiety disorders (Psychopharmacology 4th Generation of progress Chapter 21, p. 227 and 237, Chapter 111, p. 1317-1318 and 1320);
Mood disorders (Psychopharmacology 4th Generation of progress Chapter 80, p. 921-928; and
Substance abuse (Psychopharmacology 4th Generation of progress Chapter 25, p. 283 and 292, Chapter 66, p. 759-760, Chapter 147, p. 1725 (see also Nisell et al, "Systemic Nicotine-Induced Dopamine Release in the Rat Nucleus Accumbens is Regulated by Nicotinic receptors in the Ventral Tegmental Area; *Synapse* (1994) 16: 36-44). Chapter 149, p. 1745-1747 and 1751-1752). Drugs abused by humans preferentially increase synaptic dopamine concentrations in the mesolimbic system of freely moving rats Di Chiara et al *Proc Natl Acad Sci USA* 85, 5274, 1988. Drug addiction as a disorder of associative learning. Role of nucleus accumbens shell/ extended amygdala dopamine *Ann N.Y. Acad Sci* 877, 461, 1999.

As shown by these references, the claimed conditions are recognized in the art as diseases which concern dopaminergic neurotransmission Furthermore, pharmacological interaction with dopaminergic neurotransmission is widely believed to be useful in the treatment of several CNS disorders, which are not generally believed to be directly caused by disruptions in dopaminergic neurotransmission. For example, the symptoms of Huntington's disease and other movement disorders can be treated with dopaminergic agents due to the involvement of dopamine in motor functions—(see Psychopharmacology 4th Generation of progress, Chapter 26, p. 295-301). Likewise, it is known that cognitive disorders (see Psychopharmacology 4th Generation of progress Chapters 25, p. 292, Chapter 120, p. 1417 and 1420, Chapter 123, p. 1447 and 1452 and 1455-1457) autism (see Psychopharmacology 4th Generation of progress Chapter 142, p. 1653 and 1661), attention-deficit hyperactivity disorders (see Psychopharmacology 4th Generation of progress Chapter 141, p. 1643 and 1649-1650), sexual disorders (see Psychopharmacology 4th Generation of progress Chapters 65, p. 743-746 and Chapter 22, p. 245 and 254) and eating disorders (see Psychopharmacology 4th Generation of progress Chapters 137, p. 1600, Chapter 138, p. 1609-1610 and 1612) may be treated with agents strengthening dopaminergic transmission. Thus, the above references support the argument that the compounds of the invention would be useful in the treatment of such diseases.

It is widely recognised that inhibition of the HERG channel can induce severe cardiac side-effects, including lethal arrhythmia (3. Cardiovasc. Electrophysiol. 15, 475, 2004; Eur. J. Pharm., 450, 37, 2002; Cardiovascular Research, 58, 32, 2003). Thus in the development of new CNS pharmaceuticals, compounds with minimal affinity at the HERG channel, leading to a wide safety margin, are sought.

Methods of Preparation

The compounds of the invention may be prepared as outlined below in Schemes 1-2. However, the invention is not limited to these methods. The compounds may also be prepared as described for structurally related compounds in the prior art. The reactions can be carried out according to standard procedures[1,2] or as described in the working examples. The starting materials for the processes described in the present application are known or may readily be prepared by conventional methods from commercially available chemicals.

Persons skilled in the art will appreciate that, in order to obtain compounds of the invention in an alternative and in some occasions, more convenient manner, the individual process steps mentioned hereinbefore may be performed in a different order, and/or the individual reactions may be performed at a different stage in the overall route (i.e. chemical transformations may be performed upon different intermediates to those associated hereinbefore with a particular reaction).

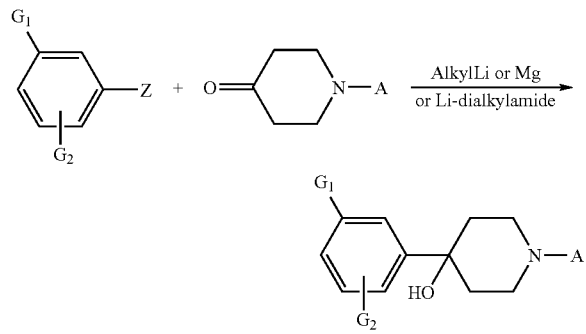

Scheme 1

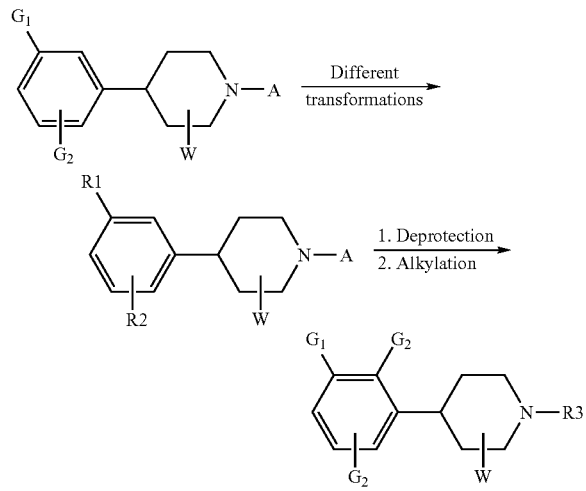

Scheme 2

The substituent Z is a leaving group, G1 is R1 or a group that can be transformed into R1, G2 is R2 or a group that can be transformed into R2, and A is alkyl hydrogen or a protecting group. W is a hydroxyl group, or a group which can be transformed into a hydroxyl group. R1, R2 and R3 are as defined above.

Ref.
1. Comprehensive Organic Transformations: A Guide to Functional Group Preparations
   Richard C. Larock, 22 October 1999 Wiley-VCH
   ISBN: 0471190314
2. March's Advanced Organic Chemistry: Reactions, Mechanisms, and Structure, 5th Edition.
   Michael B. Smith, Jerry March, Jan. 15, 2001 Wiley-Interscience
   ISBN: 0471585890

As used herein the term $C_1$-$C_4$ alkyl refers to an alkyl containing 1-4 carbon atoms in any isomeric form. The various carbon moieties are defined as follows: Alkyl refers to an aliphatic hydrocarbon radical and includes branched or unbranched forms such as methyl, ethyl, n-propyl, i-propyl, n-butyl, i-butyl, s-butyl, t-butyl. The term "allyl" refers to the group —$CH_2$—CH=$CH_2$.

The term "patient" used herein refers to an individual in need of the treatment according to the invention.

The term "treatment" used herein relates to both treatment in order to cure or alleviate a disease or a condition and to treatment in order to prevent the development of a disease or a condition. The treatment may either be performed in an acute or in a chronic way.

Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as toluensulfonate, methanesulfonate, fumarate, hydrochloride, hydrobromide, hydroiodide, nitrate, acetate, lactate, citrate, acid citrate, tartrate, bitartrate, aliphatic, alicyclic, aromatic or heterocyclic carboxylate, succinate, maleate, fumarate, gluconate, glycolate, saccharate, ascorbate, acetate, propionate, benzoate, pyruvate, pamoate [i.e., 1,1'-methylene-bis-(2-hydroxy-3-naphthoate)], phosphate, acid phosphate, sulphate or bisulfate salts. These salts are readily prepared by methods known in the art. It is also to be understood that compounds of the present invention can exist in solvated as well as unsolvated forms such as, e.g, hydrated forms.

The pharmaceutical composition containing a compound according to the invention may also comprise substances used to facilitate the production of the pharmaceutical preparation or the administration of the preparations. Such substances are well known to people skilled in the art and may for example be pharmaceutically acceptable adjuvants, carriers and preservatives.

In clinical practice the compounds used according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules. Examples of tablet and capsule formulations suitable for oral administration are given below:

| Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound | 10 |
| Lactose Ph. Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated in the clinic would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve which delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 μM of the compound is obtained.

Any chemical formula or name given herein is meant to include all stereo and optical isomers and racemates and mixtures thereof in any ratio. The various isomers can be obtained by standard methods well known to persons skilled in the art, e.g. via chromatography or fractional crystallisation. For example, cis/trans mixtures can be separated into the individual stereoisomers by stereoselective synthesis. Enantiomers or diastereomers may be isolated by separation of their mixtures, for instance by fractional crystallisation, resolution or HPLC. Alternatively separation can be afforded by derivatisation with a chiral reagent. Stereoisomers may be made by stereoselective synthesis from stereochemically pure starting materials under conditions which will not cause loss of stereochemical integrity. All stereoisomers are included within the scope of the invention.

The compounds of the present invention may be isolated in any level of purity by standard methods and purification can be achieved by conventional means known to those skilled in the art, such as distillation, recrystallization and chromatography.

The invention is further illustrated in the examples below, which in no way are intended to limit the scope of the invention.

EXAMPLE 1

4-[2-FLUORO-3-(TRIFLUOROMETHYL)PHENYL]-1-PROPYLPIPERIDIN-4-OL

To a solution of 3-bromo-2-fluorobenzotrifluoride (5.0 g, 20.5 mmol) in dry tetrahydrofurane (70 ml) at −78° C. under nitrogen, was added dropwise n-butyllithium (2.5 M in hexane, 9.0 ml, 22.5 mmol). The mixture was stirred for 1 h after which a solution of newly distilled 4-propyl-1-piperidone (2.6 g, 20.5 mmol) in dry tetrahydrofurane (30 ml) was added dropwise. The mixture was stirred at −78° C. for 30 min and then brought to ambient temperature. Water (100 ml) was added and the mixture was extracted with ethylacetate (3×100 ml). The combined organic phases was dried (MgSO4), filtered and evaporated to dryness. The oily residue was purified by flash column chromatography (ethylacetate/methanol, 1:1), to give the title compound (2.8 g, 45%). The amine was converted to the hydrochloric acid salt and recrystallized from ethanol/diethyl ether: M.p. 175-177° C. MS m/z (rel. intensity, 70 eV) 305 (M+, 5), 276 (bp), 258 (35), 191 (21), 185 (17).

EXAMPLE 2

4-[4-CHLORO-3-(TRIFLUOROMETHYL)PHENYL]-1-(2-METHOXYETHYL)PIPERIDIN-4-OL

To a mixture of 4-[chloro-3-(trifluoromethyl)phenyl]piperidin-4-ol (0.5 g, 1.79 mmol) and potassium carbonate (0.62 g, 4.47 mmol) in acetonitrile (40 ml) was added 1-bromo-2-methoxy ethane (0.17 ml, 1.79 mmol) and a small crystal of sodium iodide and the mixture was heated at reflux for 15 h. The mixture was cooled to ambient temperature, water was added (50 ml) and the phases were separated. The aqueous phase was extracted with ethylacetate (2×50 ml) and the combined organic phases was dried (MgSO4) and evaporated under reduced pressure to give an oil. Purification by flash column chromatography (ethylacetate/methanol, 1:1) gave the title compound (0.41 g, 70%). The amine was converted to the hydrochloric acid salt and recrystallized from ethanol/diethyl ether: M.p. 181-183° C. MS m/z (relative intensity, 70 eV) 337 (M+, 1), 294 (29), 292 (bp), 274 (72) 201 (29).

EXAMPLE 3

4-[2-FLUORO-3-(TRIFLUOROMETHYL)PHENYL]-1-ETHYLPIPERIDIN-4-OL

Preparation according to Example 1: 3-Bromo-2-fluorobenzotrifluoride (5.0 g, 20.6 mmol), tetrahydrofurane (50 ml), n-butyllithium (2.5 M in hexane, 9.0 ml, 22.5 mmol), 4-ethyl-1-piperidone (2.6 g, 20.6 mmol). Yield: 4.0 g. The amine was converted to the hydrochloric acid salt and recrystallized from ethanol/diethyl ether: M.p. 177-180° C. MS m/z (rel. intensity, 70 eV) 291 (M+, 18), 277 (15), 276 (bp), 258 (37), 191 (27).

EXAMPLE 4

4-[2-FLUORO-3-(TRIFLUOROMETHYL)PHENYL]-1-(2-M ETHOXYETHYL)PIPERIDIN-4-OL

Preparation according to Example 2: 4-[2-fluoro-3-(trifluoromethyl)phenyl]piperidin-4-ol (0.31 g, 1.18 mmol), potassium carbonate (0.3 g, 2.17 mmol), acetonitrile (20 ml), 1-bromo-2-methoxy ethane (0.11 ml, 1.3 mmol). Yield: (0.29 g, 76%). The amine was converted to the hydrochloric acid salt and recrystallized from ethanol/diethyl ether: M.p. 159-160° C. MS m/z (relative intensity, 70 eV) 321 (M+, 3), 277 (13), 276 (bp), 258 (24) 191 (9).

EXAMPLE 5

4-[2-FLUORO-3-(TRIFLUOROMETHYL)PHENYL]-1-BUTYLPIPERIDIN-4-OL

Preparation according to Example 2: 4-[2-fluoro-3-(trifluoromethyl)phenyl]piperidin-4-ol (0.31 g, 1.18 mmol), acetonitrile (20 ml), potassium carbonate (0.3 g, 2.9 mmol), bromobutane (0.16 ml, 1.3 mmol). Yield: 0.26 g, 70%. The amine was converted to the hydrochloric acid salt and recrystallized from ethanol/diethyl ether: M.p. 138° C. MS m/z (relative intensity, 70 eV) 319 (M+, 6), 277 (14), 276 (bp), 258 (23) 185 (9).

EXAMPLE 6

4-(2,3-DICHLOROPHENYL)-1-PROPYL-PIPERIDIN-4-OL

Preparation according to Example 2: 4-(2,3-dichlorophenyl)piperidin-4-ol (0.43 g, 1.75 mmol), acetonitrile (20 ml), potassium carbonate (0.59 g, 4.3 mmol), iodopropane (0.15 ml, 1.9 mmol). Yield: 0.29 g, 57%. The amine was converted to the hydrochloric acid salt and recrystallized from ethanol/diethyl ether: M.p. 181-183° C. MS m/z (relative intensity, 70 eV) 289 (M+, 2), 287 (M+, 4), 260 (64), 258 (bp) 240 (33).

EXAMPLE 7

4-(2,3-DICHLOROPHENYL)-1-(2-METHOXYETHYL)-PIPERIDIN-4-OL

Preparation according to Example 2: 4-(2,3-dichlorophenyl)piperidin-4-ol (0.44 g, 1.81 mmol), acetonitrile (20 ml), potassium carbonate (0.5 g, 3.6 mmol), 1-bromo-2-methoxyethane (0.17 ml, 2.0 mmol). Yield: 0.3 g, 54%. The amine was converted to the hydrochloric acid salt and recrystallized from ethanol/diethyl ether. M.p. 135-137° C. MS m/z (relative intensity, 70 eV) 305 (M+, 1), 303 (M+, 1), 260 (63), 258 (bp) 240 (31).

EXAMPLE 8

4-[4-FLUORO-3-(TRIFLUOROMETHYL)PHENYL]-1-PROPYLPIPERIDIN-4-OL

Preparation according to Example 2: 4-[4-fluoro-3-(trifluoromethyl)phenyl]piperidin-4-ol (0.4 g, 1.52 mmol), acetonitrile (20 ml), potassium carbonate (0.42 g, 3.0 mmol), iodopropane (0.18 ml, 1.82 mmol). Yield: 0.31 g, 67%. The

EXAMPLE 9

1-BUTYL-4-[4-METHYL-3-(TRIFLUOROM-ETHYL)-PHENYL]PIPERIDIN-4-OL

Preparation according to Example 2: 4-[4-methyl-3-(trifluoromethyl)phenyl]piperidin-4-ol (0.5 g, 1.93 mmol), acetonitrile (20 ml), potassium carbonate (0.53 g, 3.8 mmol), 1-bromobutane (0.20 ml, 2.1 mmol). Yield: 0.48 g, 79%. The amine was converted to the hydrochloric acid salt and recrystallized from ethanol/diethyl ether: M.p. 197-198° C. MS m/z (relative intensity, 70 eV) 315 (M+, 7), 272 (bp), 254 (48), 181 (38), 169 (25).

EXAMPLE 10

1-SEC-BUTYL-4-[2-FLUORO-3-(TRIFLUOROM-ETHYL)PHENYL]PIPERIDIN-4-OL

Preparation according to Example 2: 4-[2-fluoro-3-(trifluoromethyl)phenyl]piperidin-4-ol (0.02 g, 0.076 mmol), acetonitrile (2 ml), potassium carbonate (0.02 g, 0.14 mmol), 2-iodobutane (0.009 ml, 0.082 mmol). MS m/z (relative intensity, 70.eV) 319 (M+, 2), 290 (72), 191 (28), 177 (14), 56 (bp).

EXAMPLE 11

4-[2-FLUORO-3-(TRIFLUOROMETHYL)PHE-NYL]-1-ISOPROPYLPIPERIDIN-4-OL

Preparation according to Example 2: 4-[2-fluoro-3-(trifluoromethyl)phenyl]piperidin-4-ol (0.02 g, 0.076 mmol), acetonitrile (2 ml), potassium carbonate (0.02 g, 0.14 mmol), 2-bromopropane (0.008 ml, 0.082 mmol). MS m/z (relative intensity, 70 eV) 305 (M+, 5), 290 (79), 191 (30), 163 (18), 56 (bp).

EXAMPLE 12

4-[2-FLUORO-3-(TRIFLUOROMETHYL)PHE-NYL]-1-(3,3,3-TRIFLUOROPROPYL)PIPERIDIN-4-OL

Preparation according to Example 2: 4-[2-fluoro-3-(trifluoromethyl)phenyl]piperidin-4-ol (0.02 g, 0.076 mmol), acetonitrile (2 ml), potassium carbonate (0.02 g, 0.14 mmol), 1,1,1-trifluoro-3-iodopropane (0.010 ml, 0.082 mmol). MS m/z (relative intensity, 70 eV) 359 (M+, 20), 276 (bp), 258 (39), 191 (21), 152 (19).

EXAMPLE 13

1-(3-FLUOROPROPYL)-4-[2-FLUORO-3-(TRIFLUOROMETHYL)PHENYL]PIPERIDIN-4-OL

Preparation according to Example 2: 4-[2-fluoro-3-(trifluoromethyl)phenyl]piperidin-4-ol (0.02 g, 0.076 mmol), acetonitrile (2 ml), potassium carbonate (0.02 g, 0.14 mmol), 1-bromo-3-fluoropropane (0.010 ml, 0.082 mmol). MS m/z (relative intensity, 70 eV) 323 (M+, 2), 276 (34), 191 (15), 116 (17), 42 (bp).

EXAMPLE 14

4-(2,3-DICHLOROPHENYL)-1-ETHYL-PIPERIDIN-4-OL

Preparation according to Example 2: 4-(2,3-dichlorophenyl)piperidine (0.02 g, 0.081 mmol), acetonitrile (2 ml), potassium carbonate (0.02 g, 0.14 mmol), iodoethane (0.007 ml, 0.082 mmol). MS m/z (relative intensity, 70 eV) 275 (M+, 14), 274 (M+, bp), 260 (67), 258 (bp), 240 (23), 173 (9).

EXAMPLE 15

1-BUTYL-4-(2,3-DICHLOROPHENYL)PIPER-IDIN-4-OL

Preparation according to Example 2: 4-(2,3-dichlorophenyl)piperidine (0.02 g, 0.081 mmol), acetonitrile (2 ml), potassium carbonate (0.02 g, 0.14 mmol), bromobutane (0.009 ml, 0.082 mmol). MS m/z (relative intensity, 70 eV) 303 (M+, 2), 302 (M+, 4), 260 (65), 258 (bp), 242 (18), 240 (27).

EXAMPLE 16

4-(2,3-DICHLOROPHENYL)-1-ISOBUTYL-PIPERIDIN-4-OL

Preparation according to Example 2: 4-(2,3-dichlorophenyl)piperidine (0.02 g, 0.081 mmol), acetonitrile (2 ml), potassium carbonate (0.02 g, 0.14 mmol), 1-bromo-2-methylpropane (0.009 ml, 0.082 mmol). MS m/z (relative intensity, 70 eV) 303 (M+, 1), 302 (M+, 2), 260 (63), 258 (bp), 242 (19), 240 (29).

EXAMPLE 17

4-(2,3-DICHLOROPHENYL)-1-(3,3,3-TRIFLUO-ROPROPYL)PIPERIDIN-4-OL

Preparation according to Example 2: 4-(2,3-dichlorophenyl)piperidine (0.02 g, 0.081 mmol), acetonitrile (2 ml), potassium carbonate (0.02 g, 0.14 mmol), 1,1,1-trifluoro-3-iodopropane (0.010 ml, 0.082 mmol). MS m/z (relative intensity, 70 eV) 343 (M+, 10), 341 (M+, 15), 260 (52), 258 (82), 152 (54), 42 (bp).

EXAMPLE 18

4-(2,3-DICHLOROPHENYL)-1-(3-FLUOROPRO-PYL)PIPERIDIN-4-OL

Preparation according to Example 2: 4-(2,3-dichlorophenyl)piperidine (0.02 g, 0.081 mmol), acetonitrile (2 ml), potassium carbonate (0.02 g, 0.14 mmol), 1-bromo-3-fluoropropane (0.010 ml, 0.082 mmol). MS m/z (relative intensity, 70 eV) 307 (M+, 4), 305 (M+, 8), 260 (63), 258 (bp), 242 (20), 240 (29).

EXAMPLE 19

4-(2,3-DIFLUOROPHENYL)-1-PROPYL-PIPERIDIN-4-OL

Preparation according to Example 1: 1-Bromo-2,3-difluorobenzene (5.0 g, 25.9 mmol), tetrahydrofurane (50 ml), n-butyllithium (2.5 M in hexane, 11.4 ml, 28.5 mmol), 4-propyl-1-piperidone (3.9 ml, 25.9 mmol). Yield: 6.43 g.

MS m/z (rel. intensity, 70 eV) 255 (M+, 4), 226 (bp), 208 (32), 141 (17), 127 (16).

EXAMPLE 20

4-[2-FLUORO-3-(TRIFLUOROMETHOXY)PHENYL]-1-PROPYLPIPERIDIN-4-OL

To a solution of 1-fluoro-2-(trifluoromethoxy)benzene (1.22 g, 6.77 mmol) in dry tetrahydrofurane (30 ml) at −78° C., under nitrogen, lithium diisopropylamide (2.5 M in hexane, 3.0 ml, 7.45 mmol) was added dropwise. The mixture was stirred for 1 h after which a solution of newly distilled 4-propyl-1-piperidone (0.96 g, 6.77 mmol) in dry tetrahydrofuran (20 ml) was added drop wise. The resulting mixture was stirred at −78° C. for 30 min and then brought to ambient temperature. Water (100 ml) was added and the mixture was extracted with ethylacetate (3×100 ml). The combined organic phases was dried ($MgSO_4$), filtered and evaporated to dryness. The oily residue was purified by flash column chromatography (ethylacetate/methanol, 1:1) to give the title compound (0.83 g).

MS m/z (rel. intensity, 70 eV) 321 (M+, 5), 293 (14), 292 (bp), 274 (25), 207 (10).

Synthesis of intermediates used in the above Examples are described in the preparations below.

PREPARATION 1

TERT-BUTYL 4-[4-FLUORO-3-(TRIFLUOROMETHYL)PHENYL]-4-HYDROXYPIPERIDINE-1-CARBOXYLATE

To a mixture of magnesium (0.5 g, 20.5 mmol), activated with 1,2-dibromoethane in dry diethyl ether (30 ml), under nitrogen, was added dropwise, a solution of 5-bromo-2-fluorobenzotrifluoride (5.0 g, 20.5 mmol) in dry diethyl ether. The mixture was heated at reflux for 1 h after which a solution of 4-Boc-1-piperidone (4.9 g, 24.6 mmol) in dry diethyl ether (50 ml) was added dropwise. The reaction mixture was stirred for 5 minutes after which aqueous ammonium chloride (100 ml, saturated) was added. The residue was extracted with ethylacetate (3×50 ml) and the combined organic phases was dried (MgSO4), filtered and evaporated to dryness. The oily residue was purified by flash column chromatography (isooctane/ethylacetate, 1:1) to give the title compound (5.0 g). MS m/z (rel. intensity, 70 eV) 363 (M+, 11), 306 (29), 290(94), 289 (bp), 245 (64).

PREPARATION 2

4-[4-FLUORO-3-(TRIFLUOROMETHYL)PHENYL]-PIPERIDIN-4-OL

To a solution of tert-butyl 4-[4-fluoro-3-(trifluoro-methyl)phenyl]-4-hydroxypiperidine-1-carboxylate (4.25 g, 11.7 mmol) in methylen chloride (30 ml) was added trifluoroacetic acid (4 ml) and the solution was stirred at ambient temperature for 20 h. 1 M aqueous sodium hydroxide (50 ml) was added and the aqueous phase was extracted with methylen chloride (3×50 ml). The combined organic phases was dried (MgSO4), filtered and evaporated to dryness. The residue was purified by flash column chromatography (ethylacetate/methanol, 1:1) to give the title compound (1.28 g). MS m/z (rel. intensity, 70 eV) 263 (M+, 9), 245 (59), 244 (29), 163 (20), 56 (bp).

PREPARATION 3

TERT-BUTYL 4-[4-METHYL-3-(TRIFLUOROMETHYL)PHENYL]-4-HYDROXYPIPERIDINE-1-CARBOXYLATE

According to Preparation 1: Magnesium (0.51 g, 20.9 mmol), diethyl ether (20 ml), 5-bromo-2-methylbenzotrifluoride (5.0 g, 20.9 mmol), 4-Boc-1-piperidone (5.0 g, 25.1 mmol). Yield: 7.4 g. MS m/z (rel. intensity, 70 eV) 359 (M+, 1), 286 (11), 287(13), 241 (10), 57 (bp).

PREPARATION 4

4-[4-METHYL-3-(TRIFLUOROMETHYL)PHENYL]-PIPERIDIN-4-OL

According to Preparation 2: Tert-butyl 4-[4-methyl-3-(trifluoro-methyl)phenyl]-4-hydroxypiperidine-1-carboxylate (5.5 g, 15.3 mmol, methylen chloride (30 ml), trifluoroacetic acid (4.5 ml). Yield: 1.97 g. MS m/z (rel. intensity, 70 eV) 259 (M+, 14), 241 (84), 240 (43), 187 (19), 56 (bp).

PREPARATION 5

TERT-BUTYL 4-[4-CHLORO-3-(TRIFLUOROMETHYL)PHENYL]-4-HYDROXYPIPERIDINE-1-CARBOXYLATE

According to Preparation 1: Magnesium (0.47 g, 19.3 mmol), diethyl ether (20 ml), 5-bromo-2-chlorobenzotrifluoride (5.0 g, 19.3 mmol), 4-Boc-1-piperidone (4.6 g, 23.1 mmol). Yield: 4.3 g. MS m/z (rel. intensity, 70 eV) 379 (M+, 1), 306 (19), 305 (17), 261 (11), 57 (bp).

PREPARATION 6

4-[4-CHLORO-3-(TRIFLUOROMETHYL)PHENYL]-PIPERIDIN-4-OL

According to Preparation 2: Tert-butyl 4-[4-chloro-3-(trifluoromethyl)phenyl]-4-hydroxypiperidine-1-carboxylate (4.3 g, 11.3 mmol, methylen chloride (30 ml), trifluoroacetic acid (4.5 ml). Yield: 1.4 g. MS m/z (rel. intensity, 70 eV) 279 (M+, 28), 263 (38), 262 (30), 261 (bp), 260 (52).

PREPARATION 7

TERT-BUTYL 4-[2-FLUORO-3-(TRIFLUOROMETHYL)PHENYL]-4-HYDROXYPIPERIDINE-1-CARBOXYLATE

According to Example 1: 3-Bromo-2-fluorobenzotrifluoride (2.6 g, 10.6 mmol), tetrahydrofurane (60 ml), n-butyllithium (2.5 M in hexane, 4:6 ml, 11.5 mmol), 4-boc-1-piperidone (2.1 g, 10.6 mmol). Yield: 3.1 g. MS m/z (relative intensity, 70 eV) 363 (M+, 2), 290 (18), 289 (31), 245 (14), 57 (bp).

PREPARATION 8

4-[2-FLUORO-3-(TRIFLUOROMETHYL)PHENYL]-PIPERIDIN-4-OL

According to Preparation 2: Tert-butyl 4-[2-fluoro-3-(trifluoro-methyl)phenyl]-4-hydroxypiperi-dine-1-carboxylate (3.1 g, 8.5 mmol, methylen chloride (20 ml), trifluoroacetic acid (2 ml). Yield: 0.62 g. MS m/z (rel. intensity, 70 eV) 263 (M+, 22), 245 (96), 244 (44), 191 (25), 56 (bp).

PREPARATION 9

TERT-BUTYL 4-(2,3-DICHLOROPHENYL)-4-HYDROXYPIPERIDINE-1-CARBOXYLATE

According to Example 1: 1-Bromo-2,3-dichlorobenzene (1.0 g, 4.4 mmol), tetrahydrofurane (40 ml), n-butyllithium (2.5 M in hexane, 1.9 ml, 4.8 mmols), 4-boc-1-piperidone (0.9 g, 4.4 mmol). Yield: 0.7 g. MS m/z (relative intensity, 70 eV) 347 (M+, 1), 345 (M+, 2), 273 (17), 271 (24), 57 (bp).

PREPARATION 10

4-(2,3-DICHLOROPHENYL)PIPERIDIN-4-OL

According to Preparation 2: Tert-butyl 4-(2,3-dichlorophenyl)-4-hydroxypiperidine-1-carboxylate (3.0 g, 8.7 mmol), methylene chloride (50 ml), trifluoroacetic acid (10 ml). Yield: 0.88 g. MS m/z (rel. intensity, 70 eV) 246 (M+, 8), 245 (14), 212 (34), 210 (bp), 192 (67).

The following tests were used for evaluation of the compounds according to the invention.

In vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and a Apple Macintosh computer equipped with a digital interface board (NB DIO-24, National Instruments, USA). Each activity monitor consisted of a quadratic metal frame (W×L 40×40 cm) equipped with photobeam sensors. During measurements of behavioural activity, a rat was put in a transparent acrylic cage (W×L×H, 40×40×30 cm) which in turn was placed in the activity monitor. Each activity monitor was equipped with three rows of infrared photobeam sensors, each row consisting of 16 sensors. Two rows were placed along the front and the side of the floor of the cage, at a 90° angle, and the third row was placed 10 cm above the floor to measure vertical activity. Photobeam sensors were spaced 2.5 cm apart. Each activity monitor was fitted in an identical sound and light attenuating box containing a weak house light and a fan.

The computer software was written using object oriented programming (LabVIEW®, National instruments, Austin, Tex., USA).

Behavioural data from each activity monitor, representing the position (horizontal centre of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 4 min after the injection of test compound. Similar behavioural recording procedures were applied for drug-naïve and drug pre-treated rats. Rats pretreated with d-amphetamine were given a dose of 1.5 mg/kg i.p. 10 min before the recording session in the activity monitor. Rats pretreated with MK-801 were given a dose of 0.7 mg/kg i.p. 90 min before the recording session in the activity monitor. The results are presented as counts/60 minutes, or counts/30 minutes, in arbitrary length units. Statistical comparisons were carried out using student's t-test vs the control group. In MK-801 or amphetamine pre-treated animals, statistical comparisons were made vs the MK801 or d-amphetamine controls, respectively.

$ED_{50}$ values for reduction of amphetamine-induced hyperlocomotion are calculated by curve fitting. For most compounds, the evaluation is based on 16 amphetamine pre-treated animals over the dose range 0, 11, 33 and 100 µmol/kg s.c. in one single experiment, with complementary doses in separate experiments. Calculations are based on distance during the last 45 minutes of one hour of measurement. The distances are normalised to amphetamine-control and fitted by least square minimization to the function "End-(End-Control)/(1+(dose/$ED_{50}$)$^{Slope}$)". The four parameters are fitted with the restrictions: $ED_{50}$>0, 0.5<Slope<3, End>0% of control. To estimate confidence levels for the parameters, the fit is repeated 100 times with a random evenly distributed squared weight (0 to 1) for every measurement value. Presented $ED_{50}$-ranges cover 95% of these values.

In vivo Test: Neurochemistry

After the behavioural activity sessions, the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 µm, 50*2 mm i.d., Phenomenex) and electrochemical detection is accomplished at two potentials on glassy carbon electrodes (MF-1000, Bioanalytical Systems, Inc.). Via a T-connection the column effluent is passed to the detection cell or to waste. This is accomplished by two solenoid valves, which block either the waste or detector outlet. By not letting the chromatographic front reach the detector, better detection conditions are achieved. The aqueous mobile phase (0.4 ml/min) for the acid system contains Citric Acid 14 mM, Sodium Citrate 10 mM, MeOH 15% (v/v) and EDTA 0.1 mM. Detection potentials relative to Ag/AgCl reference is 0.45 and 0.60V. The aqueous ion pairing mobile phase (0.5 ml/min) for the amine system contains Citric Acid 5 mM, Sodium Citrate 10 mM, MeOH 9% (v/v), MeCN 10.5% (v/v), Decane Sulfonic Acid 0.45 mM, and EDTA 0.1 mM. Detection potentials relative to Ag/AgCl reference is 0.45 and 0.65V.

ED$_{50}$ values for the increase of DOPAC in striatum are calculated by curve fitting. For most compounds, the evaluation is based on 20 animals over the dose range 0, 3.7, 11, 33 and 100 µmol/kg s.c. in one single experiment. The DOPAC levels are normalised to control and fitted by least square minimization to the function "End-(End-Control)/(1+(dose/ED$_{50}$)$^{Slope}$)". The four parameters are fitted with the restrictions: ED$_{50}$>0, 0.5<Slope<3, 350<End<400 or End=200% of control (see table 1). To estimate confidence levels for the parameters, the fit is repeated 100 times with a random evenly distributed squared weight (0 to 1) for every measurement value. Presented ED$_{50}$-ranges cover 95% of these values.

In vivo Test: Oral Bioavailability

Experiments are performed 24 hours after implantation of arterial and venous catheters. Test compound is administered orally at 12.5 µmol/kg or intravenously at 5 µmol/kg using the venous catheters, n=3 per group. Arterial blood samples are then taken during eight hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following: AUC: the area under the plasma concentration versus time curve from time zero to the last concentration measured (Clast), calculated by the log/linear trapezoidal method.

The levels of test compound are measured by means of liquid chromatography-mass spectrometry (LC-MS). (Hewlett-Packard 1100MSD Series). The module include a quaternary pump system, vacuum degasser, thermostatted autosampler, thermostatted column compartment, diode array detector and API-ES spray chamber. Data handling was performed with a HP ChemStation rev.A.06.03. system. Instrument settings: MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 µm) at 20° C. The mobile phase was acetic acid (0.03%) (solvent A) and acetonitrile (solvent B). The flow rate of the mobile phase was 0.8 ml/min. The elution was starting at 12% of solvent B isocratic for 4.5 min, then increasing linearity to 60% over 4.5 min.

Extractions procedure: Plasma samples (0.25-0.5 ml) were diluted with water to 1 ml, and 60 pmol (100 µl) internal standard (−)-OSU6241 was added. The pH was adjusted to 11 by the addition of 25 µl saturated aqueous sodium carbonate. After mixing, the samples were extracted with 4 ml dichloromethane by shaking for 20 min. The organic layer was after centrifugation transferred to a smaller tube and evaporated to dryness under a stream of nitrogen. The residue was then dissolved in 120 µl mobile phase (acetic acid (0.03%): acetonitrile, 95:5) for LC-MS analysis (10 µl injected). The selective ion (MH$^+$) was monitored for each Example, and MH$^+$ 296 for (−)-OSU6241 ((3-[3-(ethylsulfonyl)phenyl]-1-propylpiperidine).

A standard curve over the range of 1-500 pmol is prepared by adding appropriate amounts of test compound to blank plasma samples.

In vitro Test: Metabolic Stability in Rat Liver Microsomes

Rat liver microsomes were isolated as described by Förlin (1980) Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex. Tox Appl Pharm. 54(3) 420-430, with minor modifications e.g. 3 mL/g liver of a 0.1 M Na/K*PO$_4$ buffer with 0.15 M KCl, pH 7.4, (buffer 1) was added before homogenisation, the homogenate was centrifuged for 20 minutes instead of 15, the supernatant was ultracentrifuged at 100.000 g instead of 105.000 g and the pellet from the ultracentrifugation was resuspended in 1 mL/g liver of 20% v/v 87% glycerol in buffer 1.

1 µL of, 0.2 or 1 mM test substance diluted in water and 10 µL 20 mg/mL rat liver micro-some were mixed with 149 µL 37° C. buffer 1 and the reaction was started by addition of 40 µL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction was stopped by addition of 100 µL pure acetonitrile. The protein precipitation was then removed by rejecting the pellet after centrifugation at 10.000 g for 10 minutes (Heraeus, Biofuge fresco) in 4° C. The test compound was analysed using HPLC-MS (Hewlett-Packard 1100MSD Series) with a Zorbax SB-C18 column (2.1*150 mm, 5 µm) using 0.03% formic acid and acetonitrile as mobile phase (gradient) or a Zorbax Eclipse XDB-C18 (3*75 mm, 3.5 µm) using 0.03% acetic acid and acetonitrile as mobile phase (gradient). The 15 min turnover was calculated as the fraction of test compound eliminated after 15 minutes, expressed in percent of 0 min levels, ie 100*[conc test compound at 0 min−concentration at 15 min]/conc at 0 min.

Preparation of liver microsomes was performed as described in Förlin (1980). Protocols for incubation with liver microsomes are referred in Crespi et Stresser (2000), and Renwick et al (2001).

Crespi C L, and D M Stressser (2000). Fluorometric screening for metabolism based drug-drug interactions. J. Pharm. Tox. Meth. 44. 325-331

Förlin L. (1980) Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex. Tox Appl Pharm. 54(3) 420-430

Renwick, A B et al. (2001). Metabolism of 2,5-bis(trifluoromethyl)-7-benzyloxy-4-trifluoromethylcoumarin by human hepatic CYP isoforms: evidence for selectivity towards CYP3A4. Xenobiotica 31(4): 187-204

Calculation of ClogP Values

Calculated octanol/water/partitioning constant values (ClogP values) have been calculated for compounds of the invention, using the Bio-Loom for Windows software, version 1.0 from BioByte Corporation (www.biobyte.com) using SMILES representations of the structures as input.

TABLE 6

ClogP values for selected compounds of the invention

| Example | ClogP |
|---|---|
| 1 | 3.24 |
| 2 | 2.73 |
| 3 | 2.71 |
| 4 | 2.36 |
| 5 | 3.76 |
| 8 | 3.24 |
| 9 | 4.12 |

The invention claimed is:

1. A compound of Formula 1:

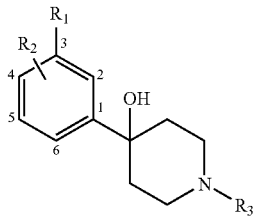

wherein:
- $R_1$ is selected from the group consisting of $OSO_2CF_3$, $OSO_2CH_3$, $SO_2CF_3$, $COCH_3$, CN, $CF_3$, $OCF_3$, F, Cl and $CF_3$;
- $R_2$ occupies the 2-position of the phenyl ring;
- $R_2$ is selected from the group consisting of F and Cl,
- $R_3$ is selected from the group consisting of $C_1$-$C_4$ alkyls, allyl, $CH_2CH_2OCH_3$, $CH_2CH_2CH_2F$, $CH_2CH_2CHF_2$ $CH_2CH_2F$, $CH_2CHF_2$ $CH_2CF_3$, 3,3,3-trifluoropropyl, and 4,4,4-trifluorobutyl;

and pharmaceutically acceptable salts thereof.

2. A compound according to claim 1, wherein $R_3$ is selected from the group consisting of n-propyl and ethyl.

3. A compound according to claim 1, wherein $R_2$ is selected from the group consisting of F and Cl and $R_3$ is selected from the group consisting of n-propyl and ethyl.

4. A compound according to claim 1, selected from the group comprising:

4-(2,3-difluorophenyl)-1-propylpiperidin-4-ol
4-(2,3-difluorophenyl)-1-ethylpiperidin-4-ol
4-(2-chloro-3-fluorophenyl)-1-propylpiperidin-4-ol
4-(2-chloro-3-fluorophenyl)-1-ethylpiperidin-4-ol
4-[2-fluoro-3-(trifluoromethyl)phenyl]-1-propylpiperidin-4-ol
1-ethyl-4-[2-fluoro-3-(trifluoromethyl)phenyl]piperidin-4-ol
4-[2-chloro-3-(trifluoromethyl)phenyl]-1-propylpiperidin-4-ol
4-[2-chloro-3-(trifluoromethyl)phenyl]-1-ethylpiperidin-4-ol
4-(3-chloro-2-fluorophenyl)-1-propylpiperidin-4-ol
4-(3-chloro-2-fluorophenyl)-1-ethylpiperidin-4-ol
4-(2,3-dichlorophenyl)-1-propylpiperidin-4-ol
4-(2,3-dichlorophenyl)-1-ethylpiperidin-4-ol
4-[2-fluoro-3-(trifluoromethoxy)phenyl]-1-propylpiperidin-4-ol
1-ethyl-4-[2-fluoro-3-(trifluoromethoxy)phenyl]piperidin-4-ol
4-[2-chloro-3-(trifluoromethoxy)phenyl]-1-propylpiperidin-4-ol
4-[2-chloro-3-(trifluoromethoxy)phenyl]-1-ethylpiperidin-4-ol.

5. A compound according to claim 1, wherein the calculated octanol/water partitioning constant value is greater than 1.0.

6. A pharmaceutical composition comprising a compound according to claim 1 and one or more pharmaceutically acceptable carriers or diluents.

* * * * *